United States Patent [19]
Grandi et al.

[11] Patent Number: 5,585,260
[45] Date of Patent: Dec. 17, 1996

[54] PSM112 PLASMID VECTOR FOR EXPRESSION IN BACILLUS SUBTILIS

[75] Inventors: Guido Grandi, Milan; Antonio Mele, Pavia, both of Italy

[73] Assignee: Eniricerche SpA, Milanese, Italy

[21] Appl. No.: 400,456

[22] Filed: Mar. 7, 1995

Related U.S. Application Data

[63] Continuation of Ser. No. 216,435, Mar. 23, 1994, abandoned, which is a continuation of Ser. No. 942,083, Sep. 8, 1992, abandoned, which is a continuation of Ser. No. 405,595, Sep. 11, 1989, abandoned, which is a continuation of Ser. No. 807,627, Dec. 11, 1985, abandoned.

[30] Foreign Application Priority Data

Dec. 11, 1984 [IT] Italy ..................... 23992/84

[51] Int. Cl.$^6$ ............. C12N 9/86; C12N 15/55; C12N 15/64; C12N 15/74
[52] U.S. Cl. .......... 435/231; 435/69.1; 435/172.3; 435/252.35; 435/370.1; 935/23; 935/29; 935/74; 935/48
[58] Field of Search ............... 435/69.1, 320.1, 435/252.35, 172.3

[56] References Cited

U.S. PATENT DOCUMENTS

| | | | |
|---|---|---|---|
| 4,626,510 | 12/1986 | Grandi | 435/317 |
| 4,663,280 | 5/1987 | Slowa | 435/69.1 |
| 4,705,750 | 11/1987 | Masakazu et al. | 435/69.1 |
| 4,711,843 | 12/1987 | Chang | 435/69.1 |
| 4,783,405 | 11/1988 | Kovacevic et al. | 435/69.1 |

FOREIGN PATENT DOCUMENTS

| | | |
|---|---|---|
| 8403519 | 9/1984 | WIPO . |
| 8500185 | 1/1985 | WIPO . |

OTHER PUBLICATIONS

Hagan, C. E., et al., 1982, Gene 1:147–151.
Hussain, M. et al, 1993, FEBS Letters, 157(1):31–36.
Mézes, P. S. F., et al., 1983, FEBS Letters, 161(2):195–200.
Ohmura, K., et al., 1984, Nucleic Acids Research 12(13):5307–5319.
Nielsen, J. B. K., et al., 1982, The Journal of Biological Chemistry, 257(8):4490–4495.
Hayashi, S., et al., 1984, The Journal of Biological Chemistry, 259(16):10448–10454.
Horinouchi, S. et al., 1982, Journal of Bacteriology, 150(2):815–825.
Date, T., et al., 1981, Proceedings of the National Academy of Sciences, U.S.A., 78(10):6106–6110.
Kreft, J., et al., 1982, in *Current Topics in Microbiology and Immunology*, 96:1–18, Published by Springer–Verlag: New York.
Ehrlich, S. D., et al., 1982, in Current Topics in Microbiology and Immunology, 96:19–27, Published by Springer–Verlag: New York.

(List continued on next page.)

*Primary Examiner*—Robert A. Wax
*Assistant Examiner*—William W. Moore
*Attorney, Agent, or Firm*—Sughrue, Mion, Zinn, Macpeak & Seas

[57] ABSTRACT pSM112 plasmid vector used for cloning heterologous proteins in *Bacillus subtilis*. A method of constructing plasmid pSM112 from plasmid pSM23 which contains the origin of replication of pUB110 and of pE194, said method comprising: a) plasmid pSM23 is linearized with XbaI restriction enzyme, b) the plasmid DNA is cyclized with T4 DNA ligase enzyme and plasmid pSM29 is isolated, c) the EcoRI-BamHI fragment of pSM29 containing the replication origin of pE194 is removed, d) the large EcoRI-BamHI fragment of pSM29 containing the replication origin of pUB110 is cyclized, and e) the plasmid pSM112 is isolated.

4 Claims, 6 Drawing Sheets

OTHER PUBLICATIONS

Sarvas, M. O., et al., 1983, Journal of Bacteriology, 155(2):657–663.

Horinouchi, S., et al., 1981, Molecular and General Genetics, 182:341–348.

Bingham, A. H. A., et al., 1982, Plasmid, 8:119–125.

Kreft, J., et al., 1983, Molecular and General Genetics, 190:384–389.

Sutcliffe, J. G., 1978, Proceedings ot the National Academy of Sciences, U.S.A. 75(8):3737–3741.

Palva, I., et al., 1982, Proceedings of the National Academy of Sciences, U.S.A., 79(18):5582–5586.

=== pUB110

≡≡≡ pE194

=== pUB110

≡≡≡ pE194

PSM112 PLASMID VECTOR FOR EXPRESSION IN BACILLUS SUBTILIS

This is a continuation of application Ser. No. 08/216,435 filed Mar. 23, 1994 (abandoned, which is a continuation of application Ser. No. 07/942,083 filed Sep. 8, 1992 (abandoned), which is a continuation of application Ser. No. 07/405,595 filed Sep. 11, 1989 (abandoned), which is a continuation of application Ser. No. 06/807,627 filed Dec. 11, 1985 (abandoned).

DESCRIPTION

The invention relates to molecular biology, more particularly to the construction of a plasmid vector of *Bacillus subtilis* capable of expressing heterologous protein genes in the aforementioned micro-organism.

It is known to prepare polypeptides and proteins such as enzymes and hormones by culturing bacteria characterised by the presence of plasmids containing the coding genes for the required proteins and polypeptides.

It is also known to construct hybrid recombinant plasmids containing the desired genes by the recombinant DNA technique of culturing bacteria containing the aforementioned plasmids so as no obtain genetic products which are usually synthesized from organisms different from those used as host cells.

In the construction of hybrid plasmids a cloning vector, e.g. a plasmid capable of replicating in the host bacterium, is combined with a heterologous DNA fragment containing a gene and/or genes for coding the desired product. According to U.S. Pat. No. 4,237,224 the preparation of recombinant DNA comprises cutting heterologous DNA by using an appropriate restriction enzyme inserting the resulting fragments in a vector, using ligase enzyme transferring the resulting hybrid molecules into host cells, and isolating (screening) the resulting clones so as to identify those containing the coding DNA for the particular protein or polypeptide of interest.

The vector used in the recombinant DNA technique comprises a cyclic DNA molecule containing sites recognized by one or more restriction enzymes used for cloning.

Accordingly the vector can be treated with a specific restriction enzyme to obtain a linear DNA molecule.

If the molecule is mixed with a sample of heterologous DNA previously cut by the same restriction enzyme in the presence of the ligase enzyme, the product is a hybrid molecule, ie. comprising the plasmid vector and a heterologous DNA fragment.

The molecule, called a "recombinant hybrid plasmid" is transferred to host cells by transformation.

The plasmid vector used in recombinant DNA techniques can be a natural vector, i.e. present in micro-organisms found in nature, or can be synthetic, i.e. constructed by genetic engineering techniques, and must be capable of reproducing itself in the host cell.

Furthermore, since a specific heterologous protein is synthesized in the host cell, the DNA needs to contain specific sequences enabling RNA polymerase to transcribe the DNA into mRNA and enabling the related ribosomes and enzymes to convert the mRNA into proteins.

These recognition sequences may differ from organism to organism. Consequently, in order to express a heterologous protein in a given host cell, it is necessary to place the structural gene of the protein under the control of recognition sequences specific to the host cell. Most work on recombinant DNA has been carried out using *Escherichia coli* cells as host cells for the production of heterologous proteins.

However, the pathogenic character of this micro-organism makes it hazardous to use products obtained thereby in sectors such as food or pharmaceuticals, and it is therefore unsuitable for industrial application.

It has therefore been thought advantageous to express heterologous genes in micro-organisms which do not have the aforementioned disadvantages.

Among these micro-organisms, *Bacillus subtilis* (*B. subtilis*) is of particular interest.

Its use in genetic engineering is particularly attractive owing to its non-pathogenic character, its conventional use in industrial fermentation processes and its capacity for secreting some of the synthesized proteins in the culture medium.

However, the use of *B. subtilis* as a potential host for the production of proteins by the recombinant DNA technique still presents numerous problems, such as the limited efficiency with which the heterologous genes are expressed. This is partly due to the lack of suitable vectors.

The invention therefore relates to a novel plasmid vector for use in recombinant DNA techniques and capable of expressing genes of heterologous proteins in *B. subtilis* with high efficiency.

To this end, according to the invention, the pSM112 plasmid vector is prepared from the pSM23 plasmid by a process comprising:

a) linearizing the pSM23 plasmid with a specific restriction enzyme, b) cyclizing the plasmid DNA with the ligase enzyme and isolating the pSM29 plasmid, c) removing the EcoRI-BamHI fragment of pSM29 containing the replication origin of pE194, d) cyclizing the large EcoRI-BamHI fragment of pSM29 containing the replication origin of pUB110, and e) isolating the pSM112 plasmid vector.

According to the invention, the pSM23 plasmid is obtained by successively coupling pE194 plasmid (BGSC 1E7) with plasmid pBR322 (ATCC 370-17) and plasmid pUB110 (ATCC 370-15) by the method described in U.S. Pat. No. 4,626,510. Plasmid pSM23, whose restriction map is shown in FIG. 1, has a single EcoRI site disposed immediately behind the ribosome recognition site (RBS) and two replication origins operating in *Bacillus subtilis*, i.e. the origin of plasmid pUB110 and the origin of plasmid pE194.

The plasmid pSM23 was deposited under the terms of the Budapest Treaty on the International Recognition of the Deposit of Microorganisms for the Purposes of Patent Procedure at the American Type Culture Collection, 12301 Parklawn Drive, Rockville, Md. 20852, USA, on Nov. 16, 1989 and has deposit no. ATCC 68179.

More particularly, the fragment corresponding to puB110 is oriented so that its BamHI restriction site is near the promotor-RBS region of pE194.

Since the presence of these two regions appears to be the cause of instability phenomena, particularly when another DNA fragment containing a functional replication origin is inserted, plasmid pSM23 has been modified so as to eliminate the replication origin of pE194 and only retain that of pUB110, which also has the advantage of being operative at high temperatures (51° C.).

To this end the intermediate plasmid pSM29 has been constructed. In its restriction map (FIG. 2) the orientation of pUB110 relative to pE194 is the opposite to that shown for plasmid pSM23.

According to the invention, therefore, plasmid pSM23, which contains the coding gene for resistance to kanamycin ($km^R$) is cut by known means, using XbaI restriction enzyme, into two fragments of different sizes: one fragment of about 4650 base pairs (bp) containing the replication origin of pUB110 and one fragment of about 3000 bp containing the replication origin of pE194.

The fragments are subsequently linked in the presence of $T_4$ ligase enzyme and the resulting mixture of ligases is used to transform cells of *B. subtilis* BGSC 1A246 made competent by known methods. The transformed cells are isolated after plating on a suitable culture medium containing 5 µg/ml of kanamycin.

By this method, only those cells containing the plasmid with the $km^R$ gene are obtained. Out of these, those colonies are selected which contain a plasmid with the BamHI site situated at a distance from the EcoRI site.

According to the invention, the pSM29 plasmid is treated with the BamHI restriction enzyme which cuts the DNA molecule at a single site, and is subsequently linked to a specific convertor. The term "convertor" means a synthetic DNA molecule for converting cohesive ends generated by a restriction enzyme into cohesive ends of another enzyme. In the present case the convertor used is BamHI-EcoRI, which has the following nucleotide sequence:

5'GATCCGAATTCG3'

GCTTAAGCCTAG

ECoRI

The resulting DNA molecule is then cut by the EcoRI restriction enzyme, producing two fragments, one having a molecular weight (MW) of $3.2 \times 10^6$D and the other containing the replication origin of pE194, MW $1.5 \times 10^6$D, the fragments subsequently being cyclized with ligase $T_4$ enzyme.

The mixture of ligased DNA is used to transform cells of *B. subtilis* BGSC 1A246, which are selected by plating on a suitable culture medium containing 5 µg/ml of kanamycin.

Out of the resulting colonies, those are selected which contain a plasmid comprising a 4950 bp fragment corresponding to the fragment containing the replication origin of pUB110.

The plasmid, denoted by the symbol pSM112, has an EcoRI site and a BamHI site disposed near the ERM-RBS recognition site, giving *B. subtilis* resistance to kanamycin and thus making them capable of replicating.

An analysis on agarose gels of the resulting bands, after cutting the resulting plasmid with the restriction enzymes EcoRI, BamHI, SstI, XbaI, HpaII and BglII, confirms the restriction map given in FIG. 3 for plasmid pSM112.

FIG. 3 also gives the sequence for the region nearest the EcoRI and BamHI sites and the ribosome recognition site.

At the EcoRI and BamHI sites it is possible to clone fragments of DNA obtained from heterologous DNA after cutting by the restriction enzymes.

The microorganism *B. subtilis* BGSC 1A246 (PSM112) was deposited on Sep. 4, 1984 at the Agricultural Research Culture Centre, North Central Region of Peoria, 1815 North University Street, Peoria, Ill. 61604, and has NRLL Accession Number B-15895.

According to the invention, as an example of the capacity of pSM112 to express heterologous genes in *B. subtilis*, we shall describe the cloning of β-lactamase genes present in the plasmid pBR322 of *E. Coli* ATCC 37017. The plasmid derived from the fusion of pSM112 with the β-lactamase gene, designated pSM119, is subsequently inserted into cells of *B. subtilis* 1A246 made competent by known methods.

An interesting feature of this cloning process is that transformed cells of *B. subtilis* cultivated in a suitable culture medium not only synthesize β-lactamase but also secrete it into the culture broth with high efficiency, thus facilitating its identification and purification.

As is known, excretion of a protein is dependent on the presence of a "leader peptide", i.e. an amino-acid sequence located at its terminal $NH_2$ extremity, when the extremity is still present in the cell. Although the molecular mechanisms are still little known, the "leader peptide" is internally linked to the cellular membrane and apparently facilitates the transit of the rest of the protein through it.

Membrane proteases are therefore also involved in cutting and separating the leader peptide from the mature protein, which is thus free in the extra-cellular environment.

It has been observed that the size of the leader peptides in proteins excreted from gram-negative bacteria is less than that for proteins from gram-positive bacteria.

In the first case the length of the leader peptides is on average between 21 and 24 amino-acids, whereas in the second case the length is from 27 to 37 amino-acids.

In order therefore to obtain excretion of heterologous proteins from gram-positive bacteria, more particularly *B. subtilis*, by recombinant DNA techniques, it appears necessary to put the protein-coding gene under the control of a leader peptide which is specific for gram-positive bacteria.

In British patent application 2 091 268, β-lactamase of pBR322 is expressed and secreted by *B. subtilis* by fusing the DNA coding sequence for mature β-lactamase with the DNA sequences which regulate expression and with the DNA sequences which code for the leader peptide which allows excretion of the α-amylase of *B. amyloliquefaciens*.

According to the invention, it has been found that β-lactamase of *E. coli* can be excreted from *B. subtilis* with high efficiency by using the leader peptide of the protein itself.

According to the invention, pSM119 hybrid plasmid is obtained by known methods by inserting in the pSM112 plasmid vector the DNA fragment containing the pBR322 β-lactamase gene of *E. coli* after removing the small EcoRI-BamHI fragment from pSM112.

The fragment containing the β-lactamase gene is isolated from pBR322 after positioning an EcoRI site in front of the ATG of the β-lactamase gene, using the "in vitro mutagenesis" technique described by M. J. Zoller et al., in Nucleic Acids Research 10 (1982) 6487–6500 and substituting the PvuII site of pBR322 with a BamHI site.

The β-lactamase gene is easily isolated by this method, after digesting pBR322 with EcoRI and BamHI restriction enzymes.

The mutated plasmid, called pSM115, obtained by the method shown in FIG. 5 contains the entire sequence of the precursor of β-lactamase and the replication origin of pBR322. The aforementioned pSM115 plasmid gives *E. coli* resistance to Ampicillin and also has an EcoRI site immediately in front of the ATG of the β-lactamase gene.

This plasmid is cut by the EcoRI and BamHI restriction enzymes, generating two fragments of different sizes, the large EcoRI-BamHI fragment (about 2150 BP) being inserted in the pSM112 vector so as to form a hybrid plasmid called pSM119.

The hybrid plasmid pSM119 is then inserted into cells of suitably prepared *B. subtilis* BGSC 1A246 and the transformed cells are isolated by plating on a culture medium containing 5 µg/ml of kanamycin.

This method is used for isolating clones containing the hybrid plasmid pSM119 which has the gene coding for resistance to kanamycin.

The microorganism *B. subtilis* BGSC 1A246 (pSM119) was deposited on Sep. 4, 1984 at the Agricultural Research Culture Centre, North Central Region of Peoria Ill. (USA), and has NRLL Accession Number B-15896.

If the cloned gene is to be capable of expressing itself, an essential condition is that its ATG is positioned very near the 5' end of the fragment inserted in the vector, so as to maintain a space of 5 to 10 bases between the conversion initiation sequence and the ribosome recognition site. More particularly, in the construction of pSM119 described here, the distance is 6 bases.

FIG. 7 shows the restriction map of pSM119 and the nearest sequence of the ATG of the β-lactamase gene. According to the invention, cells of *B. subtilis* BGSC 1A246 (pSM119) are cultured in a liquid culture medium containing sources of carbon, nitrogen essential organic salts and trace-elements chosen from those known to a skilled artisan, and the production of β-lactamase is measured seperately in the cutline broth and in the cellular extract.

The enzyme is secreted in the culture medium with high efficiency (75%), indicating that the leader peptide of the precursor of β-lactamase is recognized and used by the *B. subtilis* secretion mechanism.

The following experimental examples are illustrative and do not limit the invention.

EXAMPLE 1

Construction of plasmid pSM29

0.3 μg of plasmid pSM23 were suspended in 20 μl of a solution containing 6 mM of Tris (hydroxymethyl) hydrochloride (Tris-HCl) pH 7.4, 100 mM NaCl and 6 mM MgCl$_2$ and were cut by 0.3 units (U) of XbaI(BRL) restriction enzyme. The mixture was incubated at a temperature of 37° C. for 1 hour. The reaction was stopped by adding an equal volume of phenol which was subsequently extracted from the aqueous phase with ether.

The linear plasmid DNA was precipitated at a temperature of −20° C. for one night after suspending it in 1/10 by volume of 3M sodium acetate and 2.5 volumes of 95% ethanol.

The precipitated DNA was separated from the reaction mixture by centrifuging at 11,000 rpm for 10 minutes. The precipitate was re-suspended in 10 μl of a solution containing 50 mM of Tris-HCl (pH 7.5), 10 mM of MgCl$_2$, 1M of dithiothreitol and 0.5 M of adenosine triphosphate (ATP) and was cyclized with 0.5 U of T$_4$ DNA ligase (BRL) enzyme at ambient temperature (20°–25° C.) for 4 hours.

The entire ligase mixture was then used to transform cells of *Bacillus subtilis* BGSC 1A246 prepared as described by D. Dubnau et al. (J. Mol. Biol. 56 (1971) 209–221).

The transformed cells were selected by plating on DIFCO Tryptose Blood agar Base (TBAB) medium containing 5 μg/ml kanamycin.

By operating in this manner, the only product was cells of *B. subtilis* containing the plasmid containing the kanamycin-resistance gene.

Plasmids were extracted and purified from 10 Km$^R$ colonies by the rapid extraction method described by Rodriguez et al in "Recombinant DNA techniques: an introduction" pp. 164–165 (1983) ADDISON-Wesvey Publishing Company, and were compared with the DNA from plasmid pUB110 by electrophoresis on agarose gels.

Figure 1:
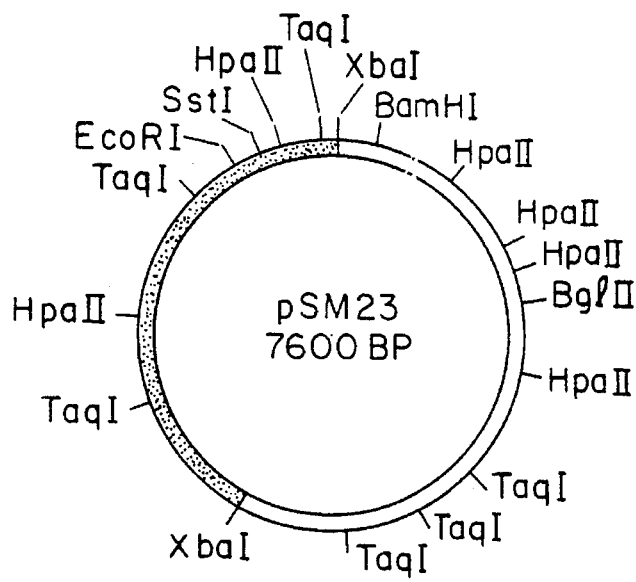
FIG. 1 Restriction map of plasmid pSM23
Figure 2:
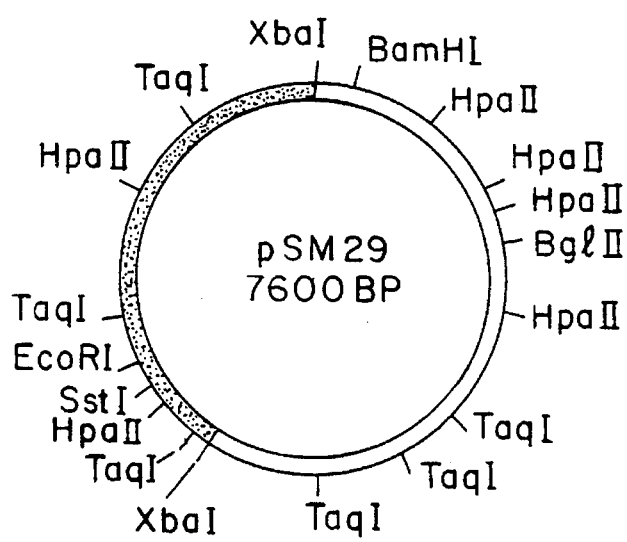
FIG. 2 Restriction map of plasmid pSM29

Two of the ten examined plasmids, after treatment with EcoRI and BamHI restriction enzymes, had two bands of about 2740 and 4890 bp each, in accordance with the fact that the smaller fragment XbaI(pE194) is inserted in the opposite direction from pSM23. One of the two plasmids was purified and called pSM29 (FIG. 2)

EXAMPLE 2

Elimination of the fragment containing the replication origin of pE194 and construction of plasmid pSM112

1 μg of plasmid pSM29 obtained as described in Example 1 was suspended in 50 μl of a solution containing 6 mM Tris-Cl (pH 7.9), 150 mM NACl 6 mM MgCl$_2$ and was treated with 1 U of BamHI (BRL) restriction enzyme at a temperature of 37° C. for 1 hour.

At the end of this time, the reaction was stopped by adding an equal volume of phenol, which was subsequently extracted from the aqueous phase with ether.

The plasmid DNA was precipitated after adding 1/10 by volume of 3M sodium acetate and 2.5 volumes of 95% ethanol, maintaining the solution at a temperature of −70° C. for 10 minutes.

The precipitate was recovered from the solution by centrifuging and washed with 70% ethanol and dried in vacuo.

The resulting plasmid DNA was resuspended in 10 μl of a solution containing 60 mM Tris-HCl (pH 7.6), 10 mM MgCl$_2$, 15 mM dithiothreitol, 1 mM spermidine and 1 mM ATP and was mixed with 10 μl of a solution having the same composition as described hereinbefore and containing 160 mg of BamHI-EcoRI (WORTHINGTON) convertor pretreated with 12 U of kinase T4 (BIOLABS) enzyme at 37° C. for 1 hour and at 65° C. for 5 minutes as described by the supplying firm.

The resulting mixture, after adding 0.5 U of T4 DNA ligase enzyme, was incubated at a temperature of 14° C. overnight. At the end of this period, the reaction was stopped by incubating at the temperature of 65° C. for 5 minutes. After adding 35 μl of H$_2$O, 5 μl of 5 M NaClO and 50 μl of isopropanol, the solution was incubated at 37° C. until the high molecular-weight DNA had completely precipitated.

The precipitated DNA was separated from the solution by centrifuging at 10,000 rpm for 10 minutes, washed with 70% ethanol, dried in vacuo and re-suspended in 20 μl of a solution containing 100 mM Tris-HCl (pH 7.5), 50 mM NaCl and 5 mM MgCl$_2$.

After adding 20 U of EcoRI restriction enzyme the solution was incubated at 37° C. for 2 hours and subsequently at 65° for 5 minutes.

The DNA was then precipitated out of solution as described previously and, after pelleting and washing with water, was suspended in 10 µl of a solution containing 50 mM Tris-HCl (pH 7.5), 10 mM MgCl₂, 1 mM dithiothreitol, 1 mM ATP and 0.5 U of T4 DNA ligase.

The reaction was carried out at a temperature of 14° C. overnight.

5 µl of the ligase mixture obtained as hereinbefore was used to transform cells of B. subtilis BGSC 1A246.

The transformants were selected on plates of TBAB medium containing 5 µg/ml of kanamycin.

Figure 3:
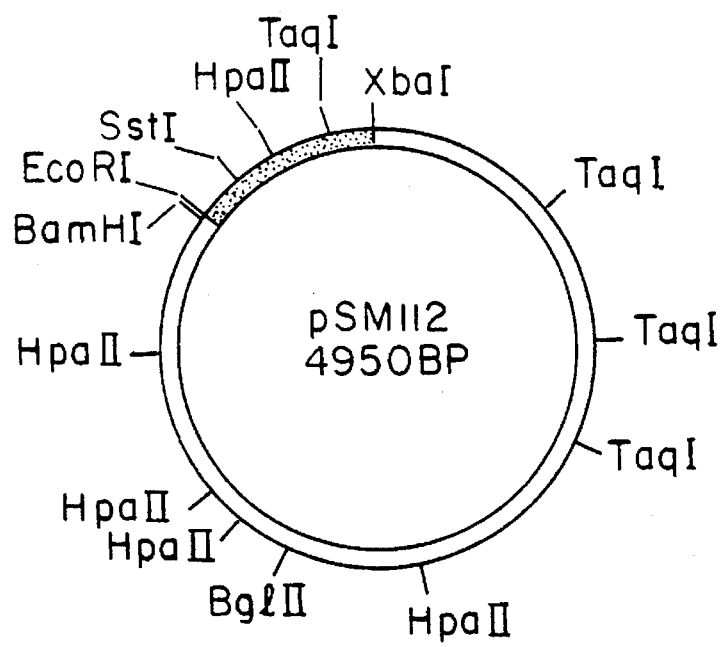
FIG. 3 Restriction map of plasmid pSM112
Figure 4:
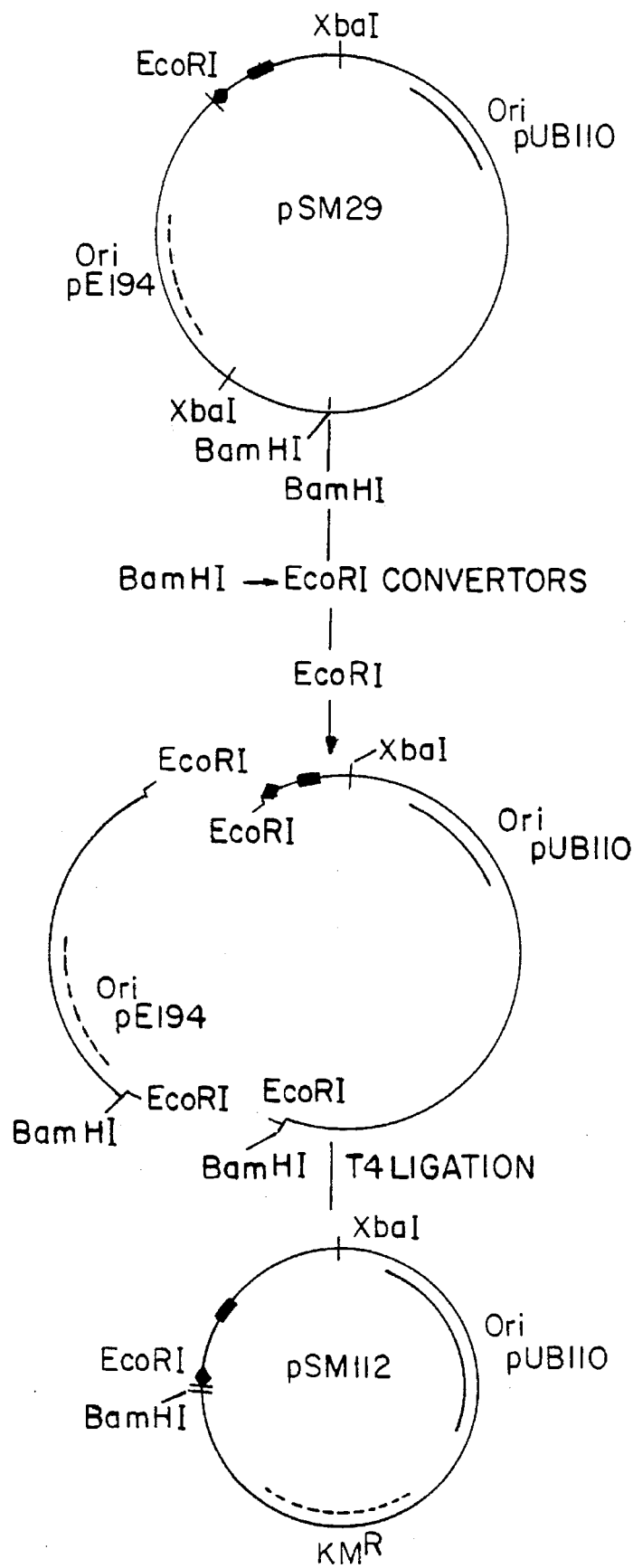
FIG. 4 Transformations for obtaining plasmid pSM112

Plasmids from 10 Km$^R$ colonies were selected by the rapid extraction method. Five of these plasmids, on analysis on agarose gel, were found to comprise a band of about 4940 bp. After cutting with EcoRI, BamHI, SstI, XbaI, HpaII, and BglII enzymes, analysis on agarose gels of the resulting bands confirmed the restriction map shown in FIG. 3 for plasmid pSM112.

EXAMPLE 3

Construction of the EcoRI site in front of the ATG of β-lactamase and isolation of the β-lactamase gene from pBR322

Cells of Escherichia coli JM83 (BRL) were cultured at 37° C. for 18 hours in 10 ml of YT medium having the following composition:

|  | g/l |
| --- | --- |
| Tryptone | 10.0 |
| Yeast extract | 5.0 |
| NaCl | 5.0 |
| Glucose | 1.0 |
| H₂0 | 1.1 | and 1 ml of M13mp9 phage solution, into which the small EcoRI PstI fragment of pBR322 had been previously introduced by known methods. The mixture was used to infect a liter of YT.

After 7 hours of growth at 37° C., the cells were separated from the phage by centrifuging and the phage in the supernatant fluid were precipitated at ambient temperature for 20 minutes by adding 250 ml of a 20% solution of polyethylene glycol (PEG) and 2.5 M NaCl.

The precipitated phase were pelleted by centrifuging and the pellet was re-suspended in 10 ml of a solution containing 10 mM Tris-HCl (pH 8.0) and 1 mM of ethylene diamino tetraacetic acid (EDTA).

A phenol extraction of phage DNA was then conducted comprising three extractions with an equal volume of phenol/chloroform (1:1) and three extractions with an equal volume of chloroform.

The phage DNA was then precipitated at a temperature of −20° C. after adding ¹⁄₁₀ by volume of 3 M sodium acetate and 2.5 volumes of 95% ethanol.

The phage DNA was pelleted by centrifuging at 10,000 rpm for 20 minutes and, after drying in vacuo, was re-suspended in a solution of 10 mM Tris-HCl pH 7.5 and 1 mM EDTA at a final concentration of 1 µg/ml.

Figure 5:
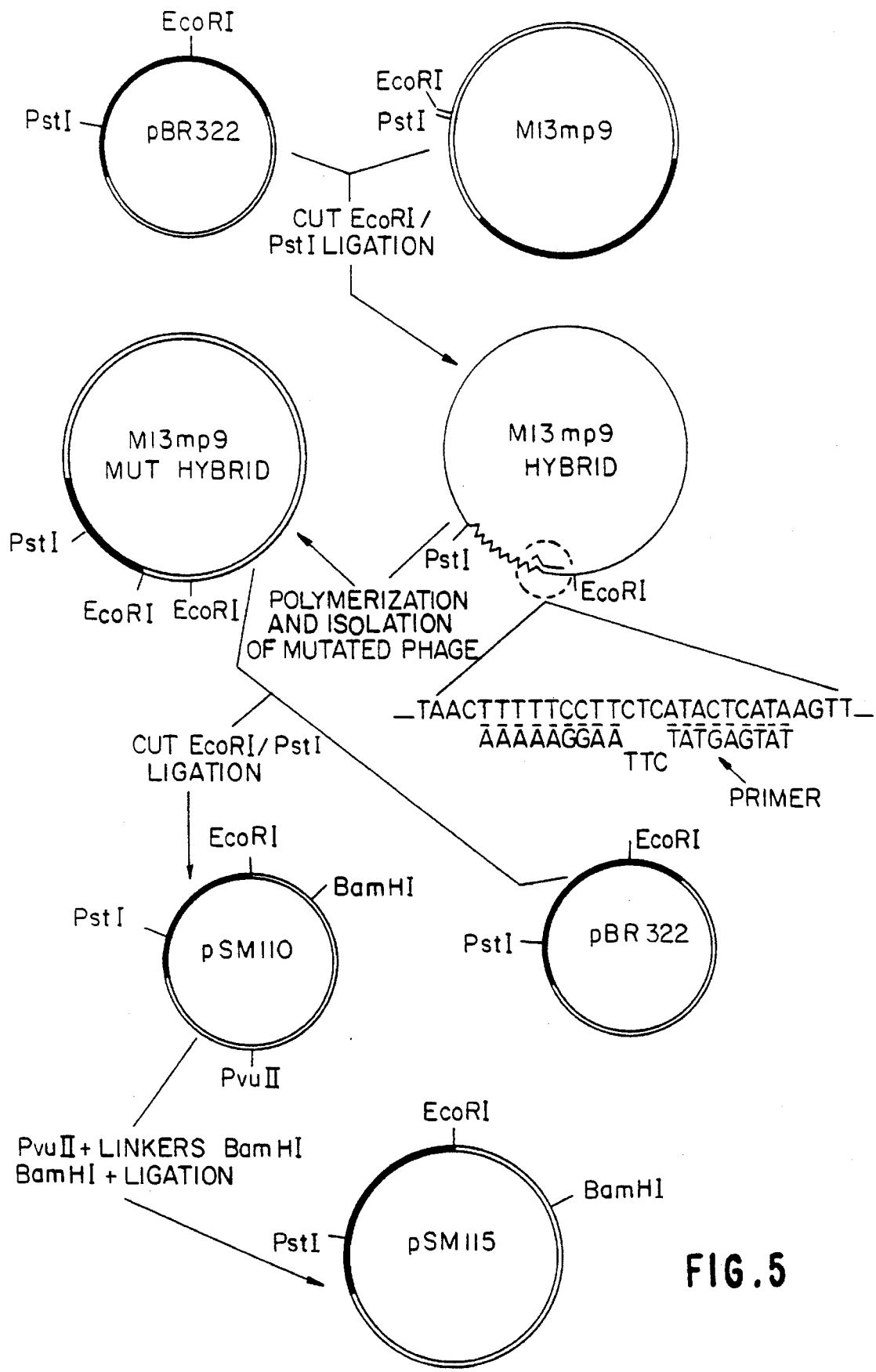
FIG. 5 Synthetic oligonucleotide and mutagenesis in vitro

2.5 µg of phage DNA and 0.2 µg of synthetic oligonucleotide phosphorylated at the 5' end, the sequence of which is shown in FIG. 5, were suspended in 10 µl of a solution containing 20 mM Tris-HCl (pH 7.5), 10 mM MgCl₂ and 50 mM NaCl and incubated for 5 minutes at 65° C. and 30 minutes at 14° C.

10 µl of a solution containing 20 mM Tris-HCl (pH 7.5) 10 mM MgCl₂, 10 mM dithiothreitol, 1 mM ATP, 1 mM deoxycytosine triphosphate (CTP), 1 mM of deoxythymidine triphosphate (TTP), 1 mM deoxylguanosine triphosphate (GTP) and 1 mM deoxyadenosine triphosphate (ATP) were added to the previously described reaction mixture and the new mixture was incubated at 14° C. for 22 hours in the presence of three units (U) of T₄ ligase and 2.5 U of E. coli DNA polymerase (Klenow fragment). At the end of this period, the reaction mixture was placed on a 0.8% agarose gel containing 0.6 µg/ml ethidium bromide and separated by applying a potential difference of 100 V.

After 3 hours the covalently closed DNA (ccDNA) visible under UV light was electro-eluted from the gel and used to transform cells of E. coli JM 17/18 (BRL) treated by the method of Mandel et al (J. Mol. Biol. 53 (1979) 159–162).

The single-stranded DNA was separated by known methods from 94 transformed clones and suspended in a solution of 10 mM Tris-HCl (pH 7.7) and 1 mM EDTA at a final concentration of 50 µg/µl. 1 µl of the suspension was absorbed by a nitrocellulose filter which was kept at 23° C. for 3 hours immersed in 10 ml of a solution containing 6×SSC (1×SSC=0.15 M NaCl, 0.015 M sodium citrate, 1 mM EDTA pH 7.2), 10×Deubardt solution (0.2% calf albumen, 0.2% polyvinyl pirrolidone, 0.2% Ficoll), 100 µg/ml of calf thymus DNA sonically treated and denatured in the presence of 1×10⁶ cpm oligonucleotide tagged with kinase and 32p ATP. After washing three times at 46° C. with 6×SSC the filter was auto-radiographed.

9 samples showed strong hybridization with the EcoRI PstI fragment of PBR322.

Analysis of the sequence of one of the DNA molecules showed the desired mutation and consequently the presence of the EcoRI site positioned in front of the ATG of the β-lactamase gene.

The next step was to purify the double-stranded form of recombinant phage DNA mutated as described by M. Zoller et al. in Nucleic Acids Research 10 (1982) 6487–6500, followed by double digestion with EcoRI and PstI restriction enzymes.

Digestion yielded 3 fragments, one of about 200 bp, corresponding to the distance between the original EcoRI site and that obtained by mutagenesis; one fragment of about 550 bp bounded by the new EcoRI site and the new PstI site located in the β-lactamase gene and one of about 7500 bp corresponding to the entire phage molecule (FIG. 5).

The 550 bp EcoRI-PstI fragment was electro-eluted from the acryl amide gel and inserted in the large EcoRI-PstI fragment of pBR322, using the T4 DNA ligase enzyme.

The ligase mixture was then used to transform cells of E. coli HB101 (BRL) which were then selected for tetracycline resistance.

A plasmid, pSM110, was isolated from one of the transformed clones. Its restriction map, shown in FIG. 5 has the expected structure giving resistance to tetracycline and Ampicillin.

EXAMPLE 4

Replacement of PvuII site by BamHI site in pSM110

0.1 µg of pSM110 were suspended in 30 µl of a solution containing 6 mM Tris-HCl (pH 7.4), 100 mM NaCl and 6 mM MgCl₂ and was cut with 0.1 unit of PvuII (BRL) restriction enzyme.

The resulting plasmid DNA was linked to the phosphorylated BamHI (Biolabs) linkers, the molar ratio between the two being 1:500.

The ligase reaction was carried out at a temperature of 14° C. for 18 hours. At the end of the reaction, the DNA was incubated with the BamHI restriction enzyme as specified by the manufacturer (Biolabs) and then precipitated by adding 1/10 by volume of 3 M sodium acetate and 2.5 volumes of ethanol.

The precipitated DNA was recovered by centrifuging at 10,000 rpm for 10 minutes and ligated to itself by $T_4$ ligase enzyme after suspension in 66 mM Tris-HCl pH 7.4, 6 mM $MgCl_2$, 10 mM dithiothreitol and 1 mM ATP at a concentration of 1 µg/ml.

The ligase mixture was then used to transform suitable cells of E. coli HB101 which were then selected for resistance to Ampicillin.

Known techniques were used to separate plasmid pSM115 from the transformed cells. The plasmid, about 2580 bp, was obtained by ligating the large BamHI-PvuII fragment of pSM110 after linking the BamHI linker to the PvuII end.

EXAMPLE 5

Insertion of the β-lactamase gene in pSM112

1 µg of pSM112 and 1 µg of pSM115 were digested with restriction enzymes BamHI and EcoRI respectively by the method given by the supplier (BRL).

The DNA was then precipitated by adding 1/10 by volume of 3 M sodium acetate and 2.5 volumes of 95% ethanol and pelleted by centrifuging.

The resulting plasmid DNA was suspended in 10 µl of a solution containing 50 mM/Tris-HCl (pH 7.5), 10 mM $MgCl_2$ and 1 mM dithiothreitol in the presence of 0.1 U of T4 DNA ligase enzyme.

5 µl of the mixture were then used to transform cells of B. subtilis BGSC 1A246 selected for resistance to kanamycin on plates of Tryptose Blood Agar Base (TBAB). DIFCO containing 5 µg/ml of kanamycin.

One of the transformed colonies was successfully isolated. It contained plasmid pSM119, which is made up of the large EcoRI-BamHI fragment of pSM112 and the EcoRI-BamHI fragement of pSM115 carrying the β-lactamase gene.

EXAMPLE 6

Production of β-lactamase from B subtilis BGSC 1A246 (pSM119)

The colony of B. subtilis containing the hybrid pSM119 plasmid was inoculated in a 250 ml Erlenmayer flask containing 25 ml of SMS (Spizien minimal salts) medium mixed with 0.5 g glucose and 50 µg/ml tryptophan, The medium had previously been sterilized at 120° C. for 15 minutes, The inoculated flask was incubated, with gentle agitation, at 37° C.

The production of β-lactamase enzyme was measured at various intervals in the cell and in the supernatant fluid as described by O'Callaghan et al. (Antimicrobial Agents and Chemotherapy 1 (1972) 283–288).

1 U of β-lactamase was defined as the quantity of enzyme required to hydrolyze a nanomol of Nitrocephin per minute at 37° C.

The sample was centrifuged at 10,000.rpm for 5 minutes and the supernatant fluid was recovered.

The cells were suspended in 25 ml of 0.1 M phosphate buffer (pH 7.0) and disintegrated by sonic treatment.

Figure 6:
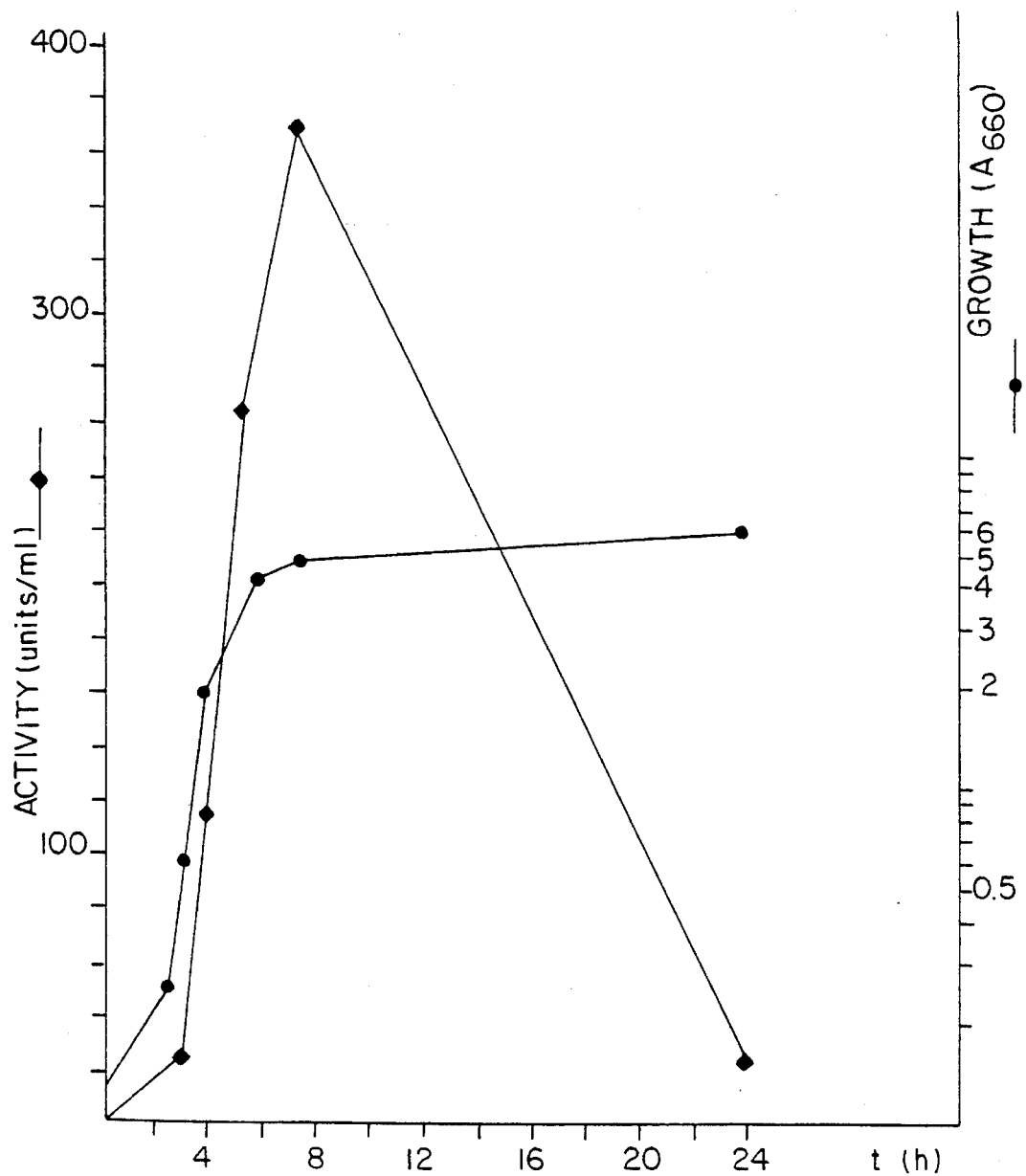
FIG. 6 β-lactamase activity measured in the supernanant fluid and cells of a culture of *B. subtilis* 1A246 (pSM119)
Figure 7:
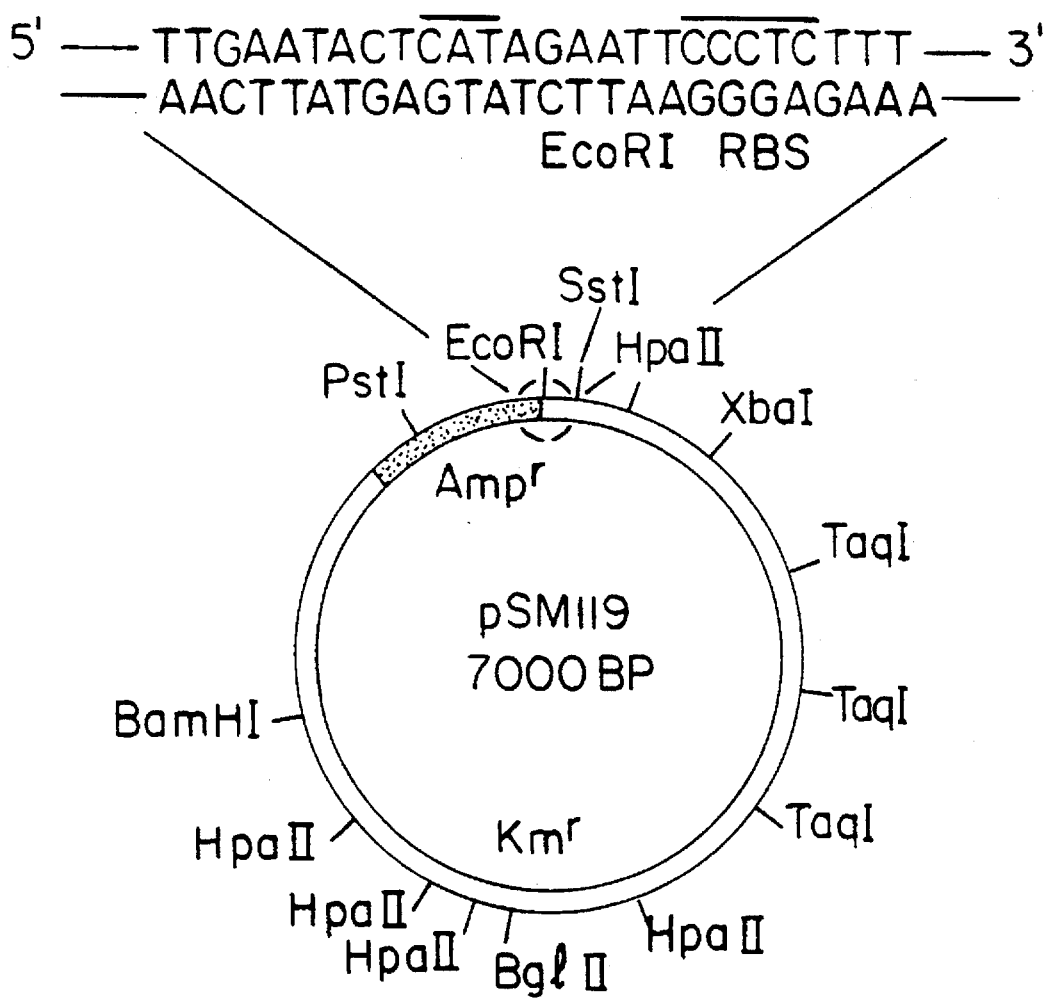
FIG. 7 Restriction map of plasmid pSM119 and the nearest sequence to the ATG of the β-lactamase gene.

FIG. 6 shows the β-lactamase activity measured in the supernatant fluid and in the cells of a culture of B. subtilis BGSG 1A246 (pSM119).

Table I hereinafter shows the production of β-lactamase in B. subtilis BGSG 1A246 (pSM119).

TABLE 1

| STRAINS | β-LACTAMASE ACTIVITY |
| --- | --- |
| B. subtilis BGSG 1A246 | 0.1 U/ml |
| B. subtilis BGSG 1A426 (pSM119) | 380 U/ml (measured in the cells) |
| B. subtilis BGSG 1A426 (pSM119) | 250 U/ml (measured in the supernatant fluid) |

We claim:

1. Hybrid plasmid vector pSM119 capable of expressing and secreting β-lactamase of Escherichia coli (E. coli) in Bacillus subtilis having NRLL accession number B-15896, said plasmid comprising, 5' to 3':
    a) a promoter and ribosome binding site from a gene coding for resistance to erythromycin derived from plasmid pE194,
    b) a β-lactamase secretion signal sequence from pBR322 of E. coli, and
    c) a β-lactamase structural gene from pBR322 of E. coli, wherein said β-lactamase structural gene and β-lactamase secretion signal sequence from pBR322 of E. coli are controlled by said promoter and ribosome binding site from a gene coding for resistance to erythromycin.

2. The microorganism Bacillus subtilis having NRLL accession number B-15896.

3. A method for preparing a hybrid plasmid pSM119 from a plasmid vector pSM112 comprising removing from said pSM112 an EcoRI-BamHI fragment and inserting therefor a DNA fragment containing an E. coli β-lactamase gene derived from pBR322.

4. A method of producing β-lactamase of Escherichia coli (E. coli) in Bacillus subtilis (B. subtilis) comprising:
    a) introducing hybrid recombinant plasmid pSM119 into B. subtilis to obtain a transformed micro-organism,
    b) culturing the micro-organism in a culture medium comprising a carbon source, a nitrogen source, essential organic salts and trace elements, and
    c) isolating said β-lactamase from the culture medium, wherein the transformed micro-organism is B. subtilis having NRLL accession number B-15896.

* * * * *